United States Patent [19]
Griessen et al.

[11] Patent Number: 5,635,729
[45] Date of Patent: Jun. 3, 1997

[54] HYDROGEN-ACTIVATED THIN FILM SWITCHING DEVICE

[75] Inventors: Ronald P. Griessen, Kortenhoef; Johannes N. Huiberts; Jan H. Rector, both of Amsterdam, all of Netherlands

[73] Assignee: U.S. Philips Corporation, New York, N.Y.

[21] Appl. No.: 646,424

[22] Filed: May 7, 1996

[30] Foreign Application Priority Data

May 30, 1995 [EP] European Pat. Off. .............. 95201408

[51] Int. Cl.$^6$ ....................................................... G02F 1/01
[52] U.S. Cl. ................... 257/2; 257/4; 257/107; 257/108; 359/248; 359/265; 359/270
[58] Field of Search .................................. 257/2, 4, 108, 257/107; 359/248, 265, 270

[56] References Cited

U.S. PATENT DOCUMENTS

| | | | |
|---|---|---|---|
| 3,961,842 | 6/1976 | Jasinski | 350/160 R |
| 4,167,309 | 9/1979 | Barclay et al. | 359/270 |
| 4,306,774 | 12/1981 | Nicholson | 359/270 |
| 4,411,497 | 10/1983 | Yamanaka et al. | 359/270 |
| 4,605,285 | 8/1986 | Fujiwara et al. | 359/270 |
| 4,649,195 | 3/1987 | Clarisse et al. | 540/143 |
| 4,828,369 | 5/1989 | Hotomi | 359/270 |
| 5,056,899 | 10/1991 | Warszawski | 359/270 |
| 5,068,062 | 11/1991 | Inata et al. | 359/241 |
| 5,086,351 | 2/1992 | Couput et al. | 359/265 |
| 5,209,980 | 5/1993 | Spindler | 428/432 |
| 5,272,359 | 12/1993 | Nagasubramanian et al. | 257/40 |
| 5,276,547 | 1/1994 | Couput et al. | 359/270 |
| 5,282,955 | 2/1994 | Leventis et al. | 205/317 |

*Primary Examiner*—Sara W. Crane
*Assistant Examiner*—David B. Hardy
*Attorney, Agent, or Firm*—John C. Fox

[57] ABSTRACT

A description is given of a switching device (1) comprising a transparent substrate (3), a reflective switching film (5) of yttrium having a thickness of 500 nm and a palladium layer (7) having a thickness of 5 nm. Using hydrogen gas at atmospheric pressure and at room temperature, a transparent, semiconductive film (5) of $YH_3$ is formed, which is converted to a metallic mirror-like film (5) of $YH_2$ by exposure to heat. The conversion of $YH_2$ into $YH_3$ is reversible and can for example be used in an optical switching element and in thin displays.

12 Claims, 1 Drawing Sheet

HYDROGEN-ACTIVATED THIN FILM SWITCHING DEVICE

BACKGROUND OF THE INVENTION

The invention relates to a switching device comprising a substrate and a metal-containing switching film. The invention also relates to applications of such a switching device.

In the relevant switching devices, the electrical and/or optical properties are governed by external influences, such as mechanical stress or electric voltage, gas pressure, relative humidity, concentration etc.

For example, electrochromic devices are well-known, in which a layer of an electrochromic material, such as $MoO_3$, is sandwiched between two transparent electroconductive electrode layers, for example, of indium-tin oxide. A layer of an $H^+$- or $Li^+$-ion-conducting material is present between an electrode and the electrochromic material. The device often also comprises a counter electrode for storing ions. The application of an electric potential of several volts across the electrodes causes the transmission of the layer packet to change. Said transmission change is reversible. Electrochromic materials are used, for example, in variable-transmission windows for buildings and anti-dazzle mirrors in cars.

A drawback of oxidic electrochromic devices is that an extensive layer stack is required for their operation. A further important disadvantage is that such materials enable only a small transmission change, and hence a small contrast, to be attained. Besides, in such devices the transition is reversibly adjustable, yet the reflection is not.

OBJECTS AND SUMMARY OF THE INVENTION

It is an object of the invention to provide, inter alia, a switching device in which the switching film can be reversibly converted from the reflective to the transparent state. Both the reflective and the transparent state must be stable. In addition, it must be possible to perform said conversion relatively rapidly at common temperatures and a common pressure. Moreover, the switching device should have a simple layer structure.

In accordance with the invention, this object is achieved by a switching device which comprises a substrate and a thin switching film including a trivalent metal which can form a hydride with hydrogen, which switching film can be reversibly switched from a metallic state to a semiconductive state by an exchange of hydrogen.

It has been found that some trivalent metals in a thin layer can form hydrides with hydrogen, which hydrides can be in the metallic state and in the semiconductive state, dependent upon the hydrogen content. In the metallic state, the metal layer, i.e. the switching film, is reflective and opaque, whereas in the semiconductive state the switching layer is transparent. In the case of a smooth substrate, the switching film forms a mirror in the metallic state.

If a thin yttrium switching film is exposed, at room temperature and at atmospheric pressure, to atomic hydrogen, first an $YH_2$ phase is formed, which has a metallic character. The $YH_2$ film thus formed is electroconductive and reflective. As the hydrogen pressure increases, an $YH_3$ phase is formed which has a semiconductive character. The $YH_3$ film formed has switched from the reflective state to the transparent state and acquires a yellow color in transmission.

The transition from the metallic dihydride phase to the semiconductive trihydride phase can be demonstrated by a Hall-effect measurement and an electric resistance measurement.

Both yttrium-hydride phases are stable at room temperature and have a range of existence around the compositions $YH_2$ and $YH_3$. The phase diagram of the YH system shows two solubility gaps, namely one between the $YH_x$ phase (α-phase with x<0.3 at room temperature) having a low H-concentration and the dihydride phase around $YH_2$ (β phase) and one between the dihydride phase and the trihydride phase around $YH_3$ (γ-phase). X-ray diffraction shows that during the absorption of hydrogen the crystal structure changes from hexagonal-hcp ($YH_x$) to cubic-fcc (dihydride phase) and subsequently to hexagonal-hcp (trihydride phase). At room temperature, the ranges of existence have a width of approximately 0.2–0.3, expressed in the molar ratio x=H/Y. In the following part of this document, the designations $YH_2$ phase and $YH_3$ phase will be used.

If molecular hydrogen is supplied to the switching film, said hydrogen must be dissociated to atomic H. Said dissociation can be promoted by providing the surface of the switching film with a thin layer of palladium having a thickness, for example, of 5 mm. At said thickness, the palladium layer is discontinuous. The layer thickness is not critical and is chosen to be in the range between 2 and 25 nm. Thin layers of 2 to 5 nm are preferred, however, because the thickness of the palladium layer determines the maximum optical transmission of the layer stack. In addition, the palladium layer protects the underlying switching film against oxidation.

A discontinuous palladium layer, or another discontinuous catalytically active layer, is preferred, in particular, if the switching device is used as an electrical switching element as a result of a change in the electrical resistance of the switching film, which change will be described hereinbelow. In this case, the electrical resistance of the switching device is governed exclusively by that of the switching film.

Apart from palladium, other catalytically active metals, such as nickel, can be provided on the switching layer.

The molecular hydrogen can be passed from a gas cylinder filled with $H_2$ to the switching film at room temperature in a simple manner. Within a few seconds the reflective metallic Y film changes into a semiconductive transparent $YH_3$ film. The bandgap of $YH_3$ is 2.3 eV. After heating, for example, to 70° C. and/or evacuation of hydrogen, the transparent $YH_3$ film is not converted to metallic Y but to a metallic $YH_2$ film which is also reflective. The latter conversion also takes place within seconds. Said conversions do not disturb or degrade the switching film.

The conversion of $YH_2$ to $YH_3$ is reversible: by supplying hydrogen, the reflective $YH_2$ film is converted at room temperature to a transparent $YH_3$ film which is converted to a reflective $YH_2$ film by heating and/or evacuation of hydrogen.

Atomic hydrogen can also be obtained in other ways, such as by means of electrochemical generation from an electrolyte, using a transparent counter electrode, for example, of indium-tin oxide. In this case, the switching device is constructed in the form of an electrochemical cell. It is alternatively possible to generate atomic hydrogen from a hydrogen plasma. In this case, a catalytically active layer, for example, of palladium is not necessary. Atomic hydrogen can also originate from another metal hydride, such as metal alloys for hydrogen storage, which are known per se.

Alternatively, the isotopes deuterium and tritium, as well as compounds with catalytically eliminable H-atoms such as methane, can be used instead of hydrogen. Hydrogen can probably also be supplied to the switching film in the form of protons, whereafter reduction to atomic hydrogen and/or formation of neutral metal hydride is brought about by electrons.

Apart from yttrium, some other trivalent metals exhibit similar phenomena. These trivalent metals are scandium, lanthanum and the rare earth metals with the atomic numbers 58 through 71. Lanthanum can be taken as an example. In a film, $LaH_2$ is metallic and reflective, whereas $LaH_3$ is semiconductive and transparent and of a red color.

The remarkable aspect of the above-mentioned trivalent metals is that, upon reaction with hydrogen, electronic states in the conduction band of the metal are reduced in energy to a very large degree. In the case of, for example, yttrium, this takes place in the 5s–4d conduction band. In the case of a hypothetical composition of $YH_1$, one full valence band is formed which has approximately 4 eV less energy than the conduction band of yttrium. As $YH_1$ comprises four outermost electrons per formula unit of which two electrons are in the full valence band at a low energy level, two electrons remain in the original conduction band of yttrium. The hypothetical $YH_1$ would be electrically conducting. In $YH_3$, three full valence bands are formed in a similar manner. As these three valence bands comprise all six outermost electrons per formula unit of $YH_3$, no conduction electrons remain; therefore $YH_3$ is a semiconductor. In $YH_2$, two full valence bands are formed in a similar manner. These two valence bands contain four out of five outermost electrons per formula unit of $YH_2$. One electron per formula unit $YH_2$ remains available for the conduction band; consequently, $YH_2$ is an electric conductor. All trivalent metals which can reversibly form trihydrides as well as non-stoichiometric hydrides with hydrogen can exhibit a metal-semiconductor transition. Said metals are also characterized by a negative enthalpy of formation of the metal hydrides, that is, they readily form hydrides.

The switching film in accordance with the invention is thin, i.e. its film thickness is less than 2 μm. The film thickness of the switching film preferably ranges between 100 and 1000 nm. As hydrogen must diffuse in the switching film, the film thickness determines the speed of conversion between the dihydride and the trihydride phase. In the case of a film thickness of the switching film of 500 nm in combination with a 5 nm thick palladium layer, the conversion of, for example, $YH_2$ to $YH_3$ and conversely takes about 5 seconds. A thinner or thicker layer will lead, respectively, to a shorter or longer conversion time.

The switching film may be composed of an alloy of the above-mentioned trivalent metals, for example Y-La, or it may be built up of two or more thin films of said metals. If desired, the switching film may be doped with maximally a few atom percent of another element such as copper. By means of these measures, the color, stability, velocity and electrical conductivity of the switching film can be influenced.

Substrates to which the switching film can be adhered can be used as the substrate for the switching film. If desired, transparent substrates can be used such as glass, quartz, diamond or aluminium oxide. The substrate may be even or curved. In the case of a polished substrate, the switching film forms a mirror in the metallic state.

The switching film is applied as a thin film to the substrate by means of conventional methods such as vacuum evaporation, sputtering, laser ablation, chemical vapour deposition or electroplating. In this respect, it is important that during and after application of the switching film, the metal of the switching film is not subject to oxidation. In a vacuum-evaporation process this is achieved by maintaining the pressure, in particular, of the residual gases, water and oxygen, at a low level below $10^{-6}$ to $10^{-7}$ mbar.

The catalytically active layer, for example, of Pd can alternatively be applied by means of one of the above-mentioned methods.

Apart from the above-mentioned optical change from the reflective state to the transparent state, a change of the electric resistance of the switching film can be observed. A controlled supply of hydrogen to the yttrium film causes an initial increase of the resistivity as the quantity of H increases in the α-phase ($YH_x$ with $x \leq 0.3$ at room temperature). The instant when demixing occurs between the α-phase and the β-phase, leading to the formation of $YH_2$, the resistivity decreases to a value below that of pure yttrium. When the γ-phase ($YH_3$) is formed, the resistivity increases by many decades. Stoichiometric $YH_3$ is a semiconductor with a bandgap of 2.3 eV.

The β-phase can also be obtained by sputtering yttrium in a hydrogen-containing atmosphere.

By virtue of the unique switch from a metallic reflective state to a transparent semiconductive state, and conversely, the switching device in accordance with the invention can be used in many applications.

By virtue of the optical effect, the switching device can be used as an optical switching element, for example as a variable beam splitter, and for controlling the illuminance or the shape of light beams in luminaires. Dependent upon the film thickness of the switching film, this film can exhibit zero transmission in the metallic state. This enables a switching device having a great contrast range to be manufactured. The switching device can be used in applications in which electrochromic layers are presently being used, such as architectural glass, sun roofs and rear-view mirrors.

The switching device in accordance with the invention can also be used as a variable transmission filter for a display screen to improve the contrast.

By making a pattern on the trivalent metal film in combination with a transparent counter electrode and an electrolyte, a reflective or transmissive thin display can be manufactured. The construction of such a display is much simpler than that of an LCD (liquid crystal display) due to the absence of an LC layer, orientation layer, retardation layer and polarization filter.

The switching film in accordance with the invention can also be used as a recording layer of an optical recording medium. A transparent $YH_3$ film can be locally converted to a reflective $YH_2$ film by means of thermal energy from a laser-light beam. If desired, the recorded information can be erased by supplying hydrogen.

As explained hereinabove, the electrical resistance of the switching film is governed by the quantity of H in the switching film. By virtue thereof, the switching device in accordance with the invention can be used as an electrical switching element and as a sensor, indicator or actuator. In a rechargeable nickel-metal-hydride battery the switching device in accordance with the invention can for example be used to indicate the cell voltage or cell pressure.

Some organic compounds, such as methane, eliminate H-atoms when they are in contact with palladium. The switching device in accordance with the invention then serves as a sensor for these organic compounds.

During the absorption of hydrogen in the switching film, an increase in thickness of approximately 11% takes place. The hydrogen absorption can be controlled electrically by means of an electrochemical cell. Thus, the switching device can be used as an actuator.

BRIEF DESCRIPTION OF THE DRAWINGS

These and other aspects of the invention will be apparent from and elucidated with reference to the embodiments described hereinafter.

In the drawings.

DESCRIPTION OF THE PREFERRED EMBODIMENTS

Exemplary embodiment 1

Figure 1:
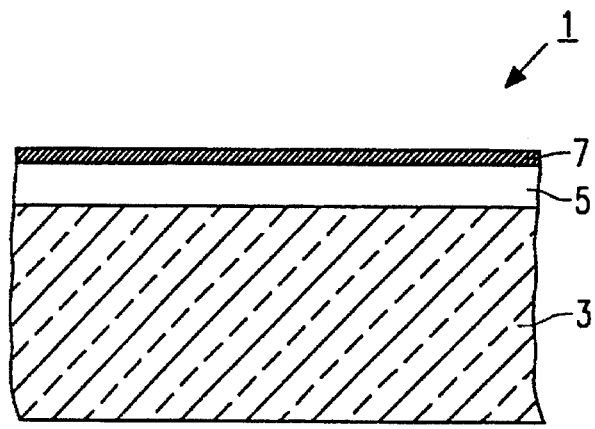
FIG. 1 is a schematic cross-sectional view of a switching device in accordance with the invention, and FIG. 2 schematically shows the phase diagram of the Y-H system and the variation of the resistivity $\rho$ (in $\mu\Omega.cm$) and the transmission I in arbitrary units as a function of the molar ratio HY of the device according to the invention.

FIG. 1 is a schematic, cross-sectional view of a switching device I in accordance with the invention. A polished, quartz substrate 3 is provided with a 500 nm thick yttrium film as a switching film 5 by means of electron-beam evaporation. The residual pressure in the evaporation apparatus is less than $10^{-7}$ mbar. The deposition rate is 0.5 nm/s. In the same apparatus, a 5 nm thick palladium layer 7 is evaporated onto the switching film 5 by means of resistance heating. If the palladium layer 7 has such a small thickness, it consists of islands which are not interconnected. Said palladium layer 7, which is invisible to the naked eye, protects the switching film 5 for at least several weeks against oxidation in air. Said switching film 5 has a metallic, mirror-like appearance and is non-transparent.

The switching film 5 is subsequently exposed to molecular hydrogen at a pressure of 1 bar ($10^5$ Pa) at room temperature in a cell which is shut off from the environment. The palladium layer 7 forms atomic H, which is subsequently absorbed in the switching film 5. After 5 seconds, the non-transparent, mirror-like switching film 5 has been converted to a transparent light yellow film having a transmission of approximately 20%. The film thus formed comprises semiconductive $YH_3$ and is semiconductive with a bandgap of 2.3 eV.

Subsequently, the cell is evacuated to a pressure of 1 mbar, whereafter air is admitted up to a pressure of 1 bar. The transparent switching film 5 is subsequently heated to 70 °C. Within 5 seconds, the switching film 5 has become mirror-like again and comprises metallically conducting $YH_2$.

The mirror-like switching film 5 of $YH_2$ can be converted to a transparent switching film 5 of $YH_3$ within 5 seconds by exposure to hydrogen. The conversion of $YH_2$ to $YH_3$, and conversely, is reversible.

Figure 2:
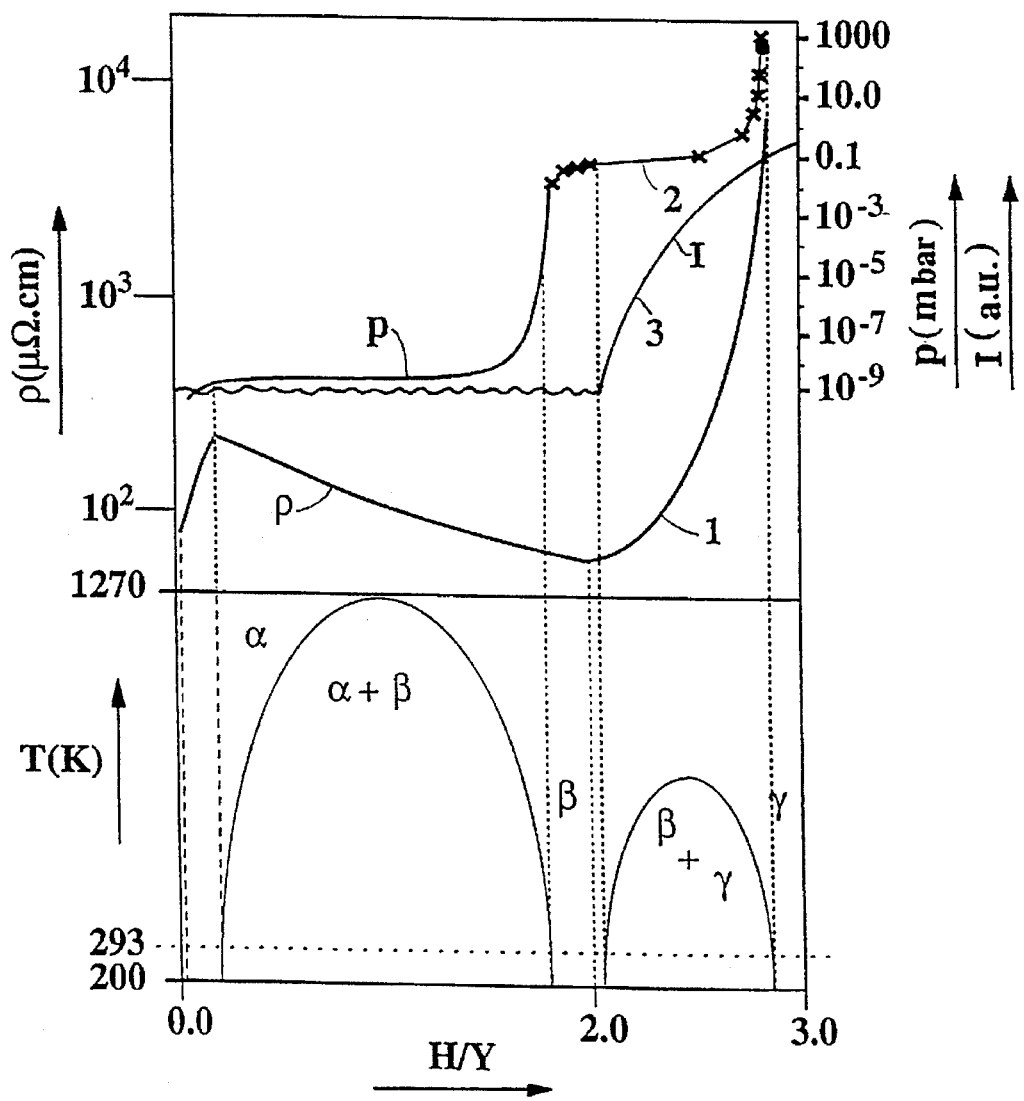

FIG. 2 schematically shows the combined phase diagram of the Y-H system and the variation of the resistivity $\rho$ (in $\mu\Omega.cm$) of the switching film 5 as a function of the molar ratio HY. Said phase diagram shows three phases $\alpha$, $\beta$ and $\gamma$, which are separated from each other by two solubility gaps. The $\alpha$-phase has a low H content and is electroconductive and reflective. The electrical resistance increases as the quantity of H increases (see curve 1). The $\beta$-phase comprises $YH_2$ and is also reflective. The electrical resistance is lower than that of the $\alpha$-phase. The $\gamma$-phase, which comprises $YH_3$, is formed as the quantity of hydrogen increases. The resistivity increases substantially. The $\gamma$-phase is semiconductive and transparent. Curve 2 in the same Figure shows the corresponding equilibrium pressure (in mbar) of hydrogen. The transition between the $\gamma$- and $\gamma$-phases is reversible by adjustment of the hydrogen pressure.

Curve 3 in the same Figure shows the corresponding transmission I (in arbitrary units a.u.) of the same device, measured with a photon energy of 1.8 eV.

The switching device in accordance with the invention can be reversibly converted from a metallic, reflective state to a semiconductive, transparent state by an exchange of hydrogen.

Exemplary embodiment 2

Exemplary embodiment 1 is repeated, using lanthanum as the switching film 5. The switching film 5 of lanthanum exhibits similar phenomena as the switching film of yttrium, however, in the semiconductive state ($LaH_3$) the switching film 5 is transparent and of a red color in transmission.

We claim:

1. A switching device comprising a substrate and a thin switching film including a trivalent metal which can form a hydride with hydrogen, which switching film can be reversibly switched from a metallic state to a semiconductive state by an exchange of hydrogen.

2. A switching device as claimed in claim 1, characterized in that the trivalent metal is selected from the group formed by Sc, Y, La and the rare earth elements, or an alloy of these metals.

3. A switching device as claimed in claim 1, characterized in that the switching film comprises yttrium.

4. A switching device as claimed in claim 3, characterized in that the switching film is reversibly switchable from a metallic, yttrium dihydride phase to a semiconductive, yttrium trihydride phase.

5. A switching device as claimed in claim 1, characterized in that the switching film has catalytically active places for the dissociation of a hydrogen-containing compound.

6. A switching device as claimed in claim 5, characterized in that the catalytically active places comprise palladium or nickel.

7. A switching device as claimed in claim 6, characterized in that the palladium is provided on the switching film in the form of a 2 to 25 nm thick layer.

8. A switching device as claimed in claim 5, characterized in that the hydrogen-containing compound is $H_2$.

9. A switching device as claimed in claim 1, characterized in that the switching film has a thickness in the range from 100 to 1000 mm.

10. A switching device as claimed in claim 1, characterized in that the switching film can be reversibly switched from a reflective, metallic state to a transparent, semiconductive state.

11. A display device incorporating at least one switching device as claimed in claim 1.

12. An optical recording device incorporating at least one switching device as claimed in claim 1.

* * * * *